United States Patent [19]

Mrozik

[11] 4,328,335
[45] May 4, 1982

[54] PROCESS FOR THE INTERCONVERSION OF C-076 COMPOUNDS

[75] Inventor: Helmut H. Mrozik, Matawan, N.J.

[73] Assignee: Merck & Co., Inc., Rahway, N.J.

[21] Appl. No.: 216,479

[22] Filed: Dec. 15, 1980

Related U.S. Application Data

[62] Division of Ser. No. 66,255, Aug. 13, 1979.

[51] Int. Cl.³ ............................................. C07H 17/08
[52] U.S. Cl. ..................................... 536/7.1; 424/180; 435/119
[58] Field of Search .................. 536/17 R; 260/343.41

[56] References Cited

U.S. PATENT DOCUMENTS 3,637,790 1/1972 Traber et al. .................... 260/455 B
4,201,861 5/1980 Mrozik et al. .................. 260/343.41

OTHER PUBLICATIONS

Wagner et al. Synthetic Organic Chemistry p. 41 John Wiley & Sons, Inc.

*Primary Examiner*—Jane T. Fan
*Attorney, Agent, or Firm*—David L. Rose; Harry E. Westlake

[57] ABSTRACT

The C-076 compounds are a series of four pairs of macrolides in which the members of each pair are homologous. The instant processes convert the C-076 A2 and B2 compounds isolated from a fermentation broth into the biologically preferred B1 and A1 compounds or into the dihydro derivatives thereof.

7 Claims, No Drawings

PROCESS FOR THE INTERCONVERSION OF C-076 COMPOUNDS

This is a division of application Ser. No. 66,255, filed Aug. 13, 1979.

BACKGROUND OF THE INVENTION

The C-076 compounds are a series of compounds which are isolated from the fermentation broth of *Streptomyces avermitilis*. The morphological characteristics of the culture, as well as the fermentation methods and processes of isolation of the C-076 compounds is described in the West German published patent Application Ser. No. 27,170,407.

The C-076 compounds have the following structure:

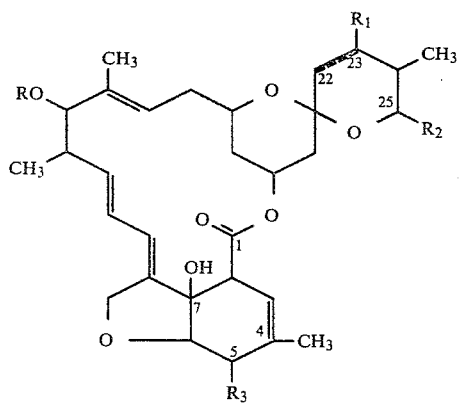

wherein R is the 4'-(α-L-oleandrosyl)-α-L-oleandrose group of the structure:

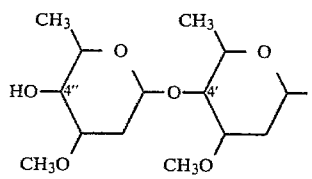

and wherein the broken line indicates a single or double bond;

$R_1$ is hydroxy and is present only when said broken line indicates a single bond;

$R_2$ is iso-propyl or sec-butyl; and $R_3$ is methoxy or hydroxy.

There are eight different C-076 compounds and they are given the designations A1a, A1b, A2a, A2b, B1a, B1b, B2a, B2b, based upon the structure of the individual compounds.

With reference to the $R_1$, $R_2$ and $R_3$ groups of the above structural formula, the individual C-076 compounds are as set forth below:

|     | $R_1$       | $R_2$      | $R_3$  |
| --- | ----------- | ---------- | ------ |
| A1a | Double Bond | sec-butyl  | —OCH$_3$ |
| A1b | Double Bond | iso-propyl | —OCH$_3$ |
| A2a | —OH         | sec-butyl  | —OCH$_3$ |
| A2b | —OH         | iso-propyl | —OCH$_3$ |
| B1a | Double Bond | sec-butyl  | —OH    |
| B1b | Double Bond | iso-propyl | —OH    |
| B2a | —OH         | sec-butyl  | —OH    |
| B2b | —OH         | iso-propyl | —OH    |

The C-076 compounds are generally isolated as mixtures of a and b components. Such compounds differ only in the nature of the $R_2$ substituent and the minor structural differences have been found to have very little effect on the isolation procedures, chemical reactivity and biological activity of such compounds.

In addition, derivatives of the C-076 compounds have been prepared. In particular, the 22,23-dihydro derivatives of the 1-series of compounds have been found to have particularly advantageous biological properties. The 22,23-dihydro derivatives are prepared by selectively hydrogenating the 22,23 unsaturated precursor. That is such compounds are prepared from the C-076 A1a/A1b and C-076 B1a/B1b pair of compounds. The 22,23 dihydro compounds and their preparation are described in European published patent application Serial No. 8300435.1. This, of course, requires that the C-076 A1a/A1b and B1a/B1b pairs be separated from the A2a/A2b and B2a/B2b pairs of compounds, and then reduced to prepare the dihydro derivatives. The main problem encountered with this procedure is that the A2a/A2b and B2a/B2b compounds remain unused, and in effect wasted.

The process of the instant invention removes this waste by converting the unused compounds into the 22,23-unsaturated precursors of the biologically preferred compounds, or into the even more biologically preferred 22,23-dihydro derivatives.

SUMMARY OF THE INVENTION

The instant invention processes for the conversion of certain C-076 compounds into other C-076 compounds and derivatives. In particular, this invention involves processes for the conversion of C-076 A2a/A2b into C-076 A1a/A1b or the 22,23 dihydro C-076 A1a/A1b; and the conversion of C-076 B2a/B2b into C-076 B1a/B1b or the 22,23 dihydro C-076 B1a/B1b. Thus, it is an object of this invention to describe the processes for the conversion of such C-076 compounds into the preferred C-076 compounds and derivatives. It is a further object of this invention to describe the protecting groups and reactions therefor which facilitate the foregoing reactions. Further processes will become apparent from reading the following description.

DESCRIPTION OF THE INVENTION

As mentioned above, the instant process achieves the conversion of the C-076 A2a/A2b and B2a/B2b into the preferred C-076 A1a/A1b and B1a/B1b compounds, and also the 22,23-dihydro derivatives thereof.

As is noted from the foregoing structure, the A2a/A2b and B2a/B2b compounds have a hydroxy group at the 23-position with the broken line indicating a single bond. The conversion of the C-076 A2a/A2b and B2a/B2b compounds into the A1a/A1b and B1a/B1b compounds thus involves the conversion of the 23-hydroxy group into 22,23 double bond. The conversion of the C-076 A2a/A2b and B2a/B2b compounds directly into the 22,23 dihydro C-076 A1a/A1b and B1a/B1b involves the removal of the 23-hydroxy and the retention of the 22,23-single bond.

The C-076 A2a/A2b compounds have, in addition to the 23-hydroxy group, a hydroxy group at the 4" position. The C-076 B2a/B2b compounds have additional hydroxy groups at the 5 and the 4" position. If this reaction is to be successfully carried out, the hydroxy group at the 5 and 4" positions must be protected, since it is an important feature of this process that only the 23-hydroxy group is permanently changed.

The preferred protecting group for the 4" and 5 positions is a trisubstituted silyloxy acetyl group. The most preferred group is the tert-butyl-dimethylsilyloxy acetyl group. The 4"-protected C-076 A2a/A2b and the 4",5-diprotected C-076 B2a/B2b compounds are prepared by combining the C-076 compound in an aprotic solvent such as methylene chloride, toluene, benzene, ethylacetate, tetrahydrofuran and the like and adding the protecting reagent which is the acid halide of the protecting group. The preferred reagent is tert-butyl-dimethylsilyloxy acetyl chloride. Also, in order to minimize side reactions, there is included in the reaction mixture a tertiary amine to react with the acid halide released during the course of the reaction. Preferred amines are pyridine and triethylamine. The tertiary amine is required in amounts equimolar to the amount of acid halide liberated, however, generally several multiples of the amine are employed. It is even possible to dispense with the solvent and use the amine in such excess that such amine, in effect becomes the solvent. The reaction is stirred at from 0° C. to the reflux temperature of the reaction mixture and is complete in from ½ to 16 hours.

Another protecting group is the trisubstituted silyl group, such as the alkyl substituted silyl group. The preferred group the tert-butyl-dimethylsilyl group. The hydroxy groups are protected by reactions with the trisubstituted silyl halide, preferably the chloride. The reaction conditions are similar to those employed for the preparation of the trisubstituted silyloxy acetyl substituent. This protecting group is removed by stirring in methanol with a catalytic amount of an acid, preferably a sulfonic acid such as p-toluene sulfonic acid. The reaction is complete in about 1-12 hours at from 0° to 50° C.

Other useful protecting groups are acyl and substituted acyl, particularly loweralkanoyl substituents such as acetyl, trifluoroacetyl, trichloroacetyl, chloroacetyl, hydroxyacetyl, phenoxyacetyl, and the like. Such acylated compounds are prepared using such acylating reagents as the halide, preferably the chloride, of the acyl group being substituted on the substrate. Additional reagents such as the anhydride or haloformate are also useful.

In those reactions employing a halide reagent, it is advantageous to include in the reaction mixture a basic compound capable of reacting with and neutralizing the hydrogen halide liberated during the course of the reaction. Tertiary amines are preferred such as triethylamine, pyridine, dimethylamino pyridine, diisopropyl ethylamine, and the like. The basic compound is required in equimolar amounts relative to the moles of hydrogen halide liberated, however, excess amounts, even using the basic compound as a solvent, are not detrimental.

The starting materials are acylated in a solvent, preferably pyridine, at from 0° C. to room temperature, preferably room temperature, and are complete in from 4-24 hours. The products are isolated using known techniques.

The acyl protecting groups are readily removed by hydrolysis of the protected compound catalyzed with a mild base in a lower alkanol at from 0° C. to room temperature, and is complete in from 1-24 hours.

With the 4"- and 5-positions protected, the 23-hydroxy group is reacted with a substituted thiocarbonyl halide of the formula:

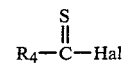

wherein Hal is a halogen such as fluorine, chlorine, bromine or iodine, although chlorine is preferred; and R4 is substituted phenoxy wherein the substituent is loweralkyl; a di-substituted amino wherein the substituents are loweralkyl.

The reaction results in the substituted thiocarbonyloxy group at the 23-position. The reaction is carried out in an aprotic solvent such as those listed above for the protection of the 4"- and 5-positions. In addition, the presence of a tertiary amine is recommended and, as above, may be used in excess to the exclusion of any other solvent. The reaction is completed in about ½ to 16 hours at room temperature with most reactions being completed in about 7 hours. The thiocarbonyl halide reagent is generally used in excess, preferably having from a 1 to 10 molar excess of such reagent. The preferred reagent for use in this reaction is the (4-methyl phenoxy) thiocarbonyl chloride.

The 23-(substituted thiocarbonyloxy) compounds are the starting materials for the reaction for the preparation of the 1-series of compounds as well as for the dihydro compounds.

The C-076 A1a/A1b and B1a/B1b compounds are prepared according to the following reaction scheme showing the partial structural formulae of the protected intermediates:

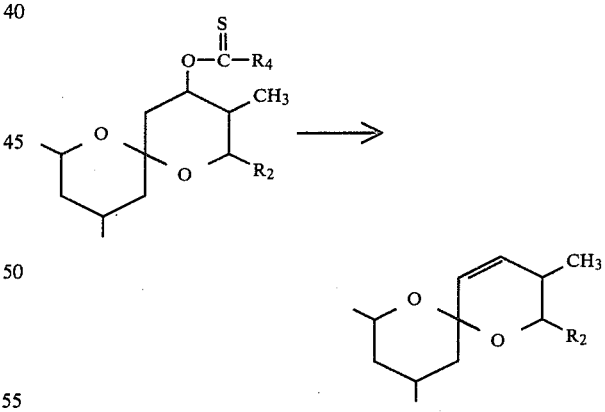

The reaction is a cis-elimination reaction of the thiocarbonyloxy leaving group and is carried out by heating the intermediate neat or in a high boiling solvent such as trichlorobenzene at about 150°-250° C. for from ½ to 3 hours. The products are isolated using techniques known to those skilled in the art. The products which are recovered are the 4",5-protected C-076 A1a/A1b and B1a/B1b compounds. The protecting groups are removed following the procedure described below.

The 23-substituted thiocarbonyloxy compound is used to directly prepare the 22,23-dihydro compound by reduction with tributyltin hydride in the presence of a free radical initiator. The reaction follows the course outlined below showing the partial structural formulae of the protected intermediates:

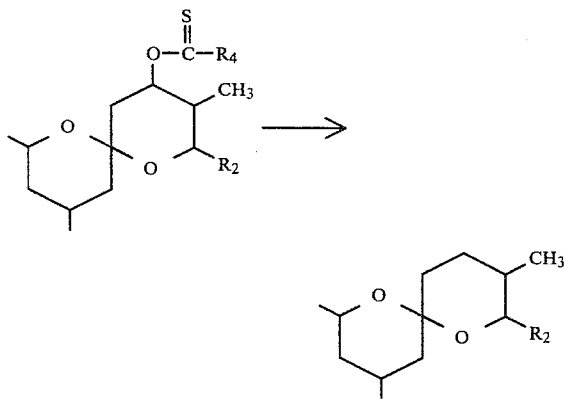

The reaction with the tributyltin hydride is carried out in an aprotic solvent such as toluene, at reflux or about 80°–110° C. and is complete in about 1–6 hours. The course of the reaction is monitored by techniques such as thin layer chromatography. If the reaction is seen to be incomplete, an additional amount of tributyltin hydride and free radical initiator is added, and the reaction heated for an additional 1–6 hours.

The preferred free radical initiator is azobisisobutyronitrile, which is employed in catalytic amounts. Other free radical initiators may be employed such as ultraviolet light or heat. If ultraviolet light is employed, the reaction temperature may be lowered, however, thin layer chromatographic analysis may reveal the need for additional reaction times. If heat is used as the free radical initiator, additional reaction may also be required. The product is isolated using known techniques.

The products recovered from the foregoing reactions having the trisubstituted silyloxy acetyl protecting group at the 4"- and 5-positions have such protecting groups removed in two steps. In the first step the protected compound is stirred at room temperature in a lower alkanol such as methanol, for about 30 minutes in the presence of p-toluene sulfonic acid. A single molar equivalent of p-toluene sulfonic acid is employed.

The product from this reaction has at the 4"- or 5-positions the hydroxy acetoxy group. That is, the tert-butyl trimethyl silyl group has been removed. Following this, the protected intermediate is treated with sodium methoxide in methanol at room temperature for from ½ to 2 hours. The hydroxy acetyl group is cleaved, leaving the hydroxy group, which product is isolated using techniques known to those skilled in this art.

Alternatively, the trisubstituted silyloxy acetyl protecting group may be removed in one step. Treatment with sodium methoxide at about room temperature for up to 6 hours will generally afford the desired unprotected product.

The compounds prepared by the processes of this invention, as well as the compounds from which they are prepared, are very active antiparasitic agents. They are, in particular, very useful as anthelmintics, ectoparasiticides, insecticides and acaricides, in human and animal health and in agriculture. When used in human and animal therapy, the compounds may be administered orally, in a solid or liquid formulation, as a unit dosage formulation or in the food or feed of the animal; or the compound may be administered as an injectable liquid solution of suspension. Dosages of from 0.025 to 0.5 mg. per kg. of animal body weight are effective. In agricultural uses, the compounds may be administered as a liquid spray or a solid dust to be applied to the plants or the soil in which they are growing; or they may be applied to the crops in bulk storage or as they are packaged or processed.

EXAMPLE 1

22,23-Dihydro C-076 B1a

A. 4",5-Di-O-(tert-butyl-dimethylsilyloxyacetyl) C-076 B2a)

In a flame dried reaction vessel containing dry nitrogen are combined 2.0 gm. of C-076 B2a, 25 ml. of diethyl ether and 2.5 ml. of dry pyridine. The solution is cooled to 0° C. in an ice bath and 8 ml. of a diethyl ether solution containing 940 mg. of tert-butyl dimethylsilyloxyacetyl chloride is added along with 600 mg. of tert-butyl dimethylsilyl chloride. The addition produces a white precipitate. The reaction mixture is stirred for 30 minutes in an ice bath after which thin layer chromatographic analysis indicates that the reaction is not yet complete. An additional 8 ml. of an ether solution containing 100 mg. of tert-butyl-dimethylsilyloxyacetyl chloride per ml. of solution is added and the reaction mixture stirred for an additional 80 minutes. Thin layer chromatographic analysis indicated the absence of starting material in the reaction mixture. 200 Ml. of cold water is added to the reaction mixture which is then extracted 5 times with 100 ml. portions of diethyl ether. The combined ether extracts are washed 7 times with 20 ml. portions of water and once with a 1:1 mixture of water and aqueous saturated sodium chloride. The ether layer is dried over magnesium sulfate and evaporated to dryness in vacuo. The residue is combined twice with diethyl ether, once with toluene and once again with diethyl ether and dried under high vacuum affording 3.2 g. of a clear white foam which is purified on a column of 175 g. of silica gel eluting with 15% ethylacetate and methylene chloride. The first 500 ml. of eluant is discarded and 20 ml. fractions are collected thereafter. Fractions 39–63 are collected affording 1.34 g. of a white foam which is indicated by mass spectrometry, and 300 mHz nuclear magnetic resonance to be 4"-5-di-O-(tert-butyl-dimethylsilyloxyacetyl) C-076 B2a.

B. 4",5-di-O-(tert-butyl-dimethylsilyloxyacetyl)-23-O-([4-methylphenoxy]thiocarbonyl) C-076 B2a 570 Mg. of 4",5-di-O-(tert-butyl dimethylsilyloxy acetyl C-076 B2a is combined with 5 ml. of pyridine and stirred under a blanket of nitrogen in an ice bath. 0.5 Ml. of O-(4-methylphenyl)chlorothioformate is added. An orange precipitate forms. The ice bath is removed and the reaction mixture is stirred for 5 hours. The reaction mixture darkens during this period. The reaction is poured into ice water and ether and saturated sodium chloride is added. The layers are separated and the aqueous layer twice more extracted with ether. The organic layers are combined and washed with water 5 times and once with saturated sodium chloride. The solution is dried over magnesium sulfate and evaporated to dryness, affording 1.59 g. of a dark brown oil. The oil is preliminarily purified on 65 g. of silica gel eluting with 700 ml. of methylene chloride through a short column. Then a 30% ethylacetate in methylene chloride eluent is used affording 700 mg. of a brown foam which is placed on 7 preparative layer chromatography plate of 1500μ of silica gel eluting twice with 20% ethyl acetate in hexane. 242 Mg. of a beige foam is recovered which is identified by mass spectrometry and nuclear magnetic resonance as 4",5-di-O-(tert-butyl-dimethyl-silyloxyacetyl)-23-O-([4methylphenoxy]thiocarbonyl) C-076 B2a.

C. 4",5-Di-O-(tert-butyl-dimethylsilyloxyacetyl)-22,23-dihydro C-076 B1a

In a flame dried reaction vessel under dry nitrogen are combined 250 mg. of 4",5-di-O-(tert-butyl-dimethyl-silyloxyacetyl)-23-O-([4-methylphenoxy)]thiocarbonyl]C-076 B2a, 7 ml. of dry toluene and 25 mg. of azobisisobutyronitrile. The reaction mixture is heated in an oil bath to 120° C. whereupon 7 ml. of a toluene solution containing 0.5 ml. of tributyltinhydride is added in 0.5 ml. portions. The reaction mixture is stirred for 60 minutes and the toluene removed under a stream of nitrogen. The reaction mixture is dissolved in methylene chloride and placed on a column of 125 g. of silica gel and eluted with methylene chloride. 325 Ml. of eluant is discarded and the eluant changed to ethyl acetate. The first 200 ml is discarded and then the column washed until the eluant shows no product. The eluent is dried and evaporated to dryness affording 310 mg. of 4",5-di-O(tert-butyl-dimethylsilyloxyacetyl)-22,23-dihydro C-076 B1a which is used as is the next reaction.

D. 4",5-di-O-(hydroxyacetyl)-22,23-dihydro C-076 B1a

310 Ml. of 4",5-di-O-(tert-butyl-dimethylsilyloxyacetyl)-22,23-dihydro C-076 B1a is combined in 60 ml. of a 1% p-toluene sulfonic acid solution of methanol and the reaction mixture stirred at room temperature for 30 minutes. The reaction is poured onto cold sodium bicarbonate solution and extracted 3 times with ether. The combined organic layers are washed 4 times with water, once with saturated sodium chloride solution, and dried over magnesium sulfate. The solution is concentrated to dryness in vacuo affording 250 mg. of solid material which is dissolved in methylene chloride and placed on two 2000μ preparative layer chromatography silica gel plates and eluted with 10% tetrahydrofuran 0.3% ethanol and methylene chloride. The slowest moving fraction contains 130 mg. of a white material which mass spectrometry and 300 mHz nuclear magnetic resonance indicate to be the product.

E. 22,23-Dihydro C-076 B1a

In a flame dried reaction vessel under dry nitrogen is combined 95 mg. of 4",5-di-O-(hydroxyacetyl) 22,23-dihydro C-076 B1a in a methanol solution of sodium methoxide prepared from 30 mg. of metallic sodium and 13 ml. of dry methanol, 10 ml. of methanol is applied to dissolve the starting material. The reaction mixture is stirred at room temperature for 30 minutes, poured onto a mixture of 100 ml. of diethyl ether and 50 ml. of water containing 0.4 ml. of acetic acid. The layers are separated and the aqueous layer extracted twice with diethyl ether. The combined ether layers are washed once with dilute sodium bicarbonate, 4 times with water and once with saturated sodium chloride solution. The organic layer is dried over magnesium sulfate and evaporated to dryness in vacuo affording 75 ml. of yellow film. It is identified by 300 mHz nuclear magnetic resonance as 22,33-dihydro C-076 B1a, which compares favorably with an authentic sample. The residue is further purified by dissolving in methylene chloride and placed on a 1000μ silica gel preparative layer chromatography plate and eluted twice with 20% ethyl acetate in methylene chloride. 73 Mg. of a white foam is obtained which is purified again on another preparative layer chromatography plate and eluted with 20% tetrahydrofuran in chloroform affording 63 mg. of a clear glass material which is identified by 300 mHz nuclear magnetic resonance as 22,23-dihydro C-076 B1a.

EXAMPLE 2

C-076 B1a

A. 4", 5-Di-O-(tert-butyl dimethylsilyloxyacetyl) C-076 B1a

10 Mg. of 4", 5-di-O(tert-butyl dimethylsilyloxyacetyl)-23-O-[(4-methylphenoxy)thiocarbonyl] C-076 B2a as obtained in Example 1B is dissolved in 0.2 ml. of 1,2,4-trichlorobenzene and heated under a stream of nitrogen in an oil bath at 200° C. for 1 hour and 45 minutes. The reaction mixture is cooled to room temperature and diluted with methylene chloride and placed on a single 1000μ silica gel preparative layer chromatography plate and eluted with 30% ethylacetate in methylene chloride affording 8.5 mg. of a clear film which is dissolved in methylene chloride and placed on 250μ silica gel preparative layer chromatography plate and eluted twice with 2.5% tetrahydrofuran, and 0.1% ethanol in methylene chloride and once with 10% ethylacetate in methylene chloride. A slower moving band affords 4 mg. of a clear film which is identified by 300 mHz nuclear magnetic resonance and mass spectroscopy to be 4", 5-di-O-(tert-butyl dimethylsilyloxyacetyl) C-076 B1a.

B. C-076 B1a/B1b

13 Mg. of 4",5-di-O-(tert-butyldimethylsilyloxyacetyl) C-076 B1a/B1b is dissolved in 1 ml. of dry methanol. 80 μL. of a previously prepared solution of sodium methoxide in methanol (from 28 mg. of sodium and 10 ml. of methanol) are added. The reaction is kept at 18° C. for 1½ hours and then added to a solution of 2 drops of acetic acid in 6 ml. of water. The product is extracted with ether, washed with water, dried and concentrated under a stream of nitrogen. Further purification by chromatography on a thin layer of silica gel gives 5 mg. of C-076 B1a/B1b. Using high pressure liquid chromatography and nuclear magnetic resonance spectroscopy, this material compares favorably with an authentic sample obtained by fermentation.

EXAMPLE 3

C-076 A1a

A. 4"-O-Acetyl-23-O[(4-methylphenoxy)thiocarbonyl] C-076 A2a

50 Mg. of C-076 A2a 4"-O-acetate is dissolved in 15 drops of dry pyridine and 3 drops of (4-methylphenyl) chlorothioformate is added at room temperature affording an immediate orange precipitate which redissolves after 10 minutes of stirring. The reaction mixture is stirred overnight at room temperature, combined with water and extracted 3 times with ether. The combined organic layers are washed 5 times with water, dried over magnesium sulfate and evaporated to dryness under a stream of nitrogen affording 100 mg. of a brown gummy material, which is dissolved in methylene chloride and placed on a 2000μ silica gel preparative layer chromatography plate and eluted with 5% tetrahydrofuran, 0.15% ethanol in methylene chloride affording 39.5 mg. of an orange solid film, which mass spectroscopy indicates to be 4"-O-acetyl-23-O[(4-methylphenoxy) thiocarbonyl] C-076 A2a.

B. C-076 A1a 4"-O-acetate

10 Mg. of 23-O[(4-methylphenoxy)thiocarbonyl] C-076 A2a 4"-O-acetate is heated at 200° C. for 20 minutes. The residue is dissolved in methylene chloride and placed on a 250μ silica gel preparative layer chromatography plate and eluted 5 times with 2.5% tetrahydrofuran 0.07% ethanol in methylene chloride. The slowest moving band is removed from the plate affording 1.7 mg. of a clear film which is identified by mass spectrometry and 300 mHz nuclear magnetic resonance as C-076 A1a 4"-O-acetate.

EXAMPLE 4

22,23-Dihydro C-076 A1a

A. 22,23-Dihydro C-076 A1a 4"-O-acetate 0.7 Ml. of dry toluene is combined with 0.1 ml. of tributyltinhydride and stirred while a solution of 5 mg. of 23-0(4-methylphenoxythiocarbonyl) C-076 A2a 4″-O-acetate in 0.3 ml. of dry toluene is added. The reaction mixture is stirred at reflux for 6 hours, the toluene removed under a stream of nitrogen while the reaction mixture is still warm and the residue diluted with methylene chloride which is placed on a single 500μ silica gel preparative layer chromatography plate and eluted with methylene chloride. The material at the origin of the plate is removed and dissolved in methylene chloride and placed on a 250μ silica gel preparative layer chromatography plate and eluted with 4% tetrahydrofuran and 0.1% ethanol in methylene chloride affording 22,23-dihydro C-076 A1a 4″-O-acetate, which is identified by mass spectrometry.

B. 22,23 Dihydro C-076 A1a

An aqueous methanolic sodium hydroxide solution is prepared from 0.065 ml. of 2.5-N aqueous sodium hydroxide, 0.5 ml. of methanol and diluted with water to a volume of 1.0 ml. 0.75 Ml. of this solution is added to a solution of 100 mg. of 4″-O-acetyl-C-076-A1a in 2.5 ml. of methanol and stirred in an ice bath for 5 hours. The usual workup and purification on thin layer silica gel plates gives 30 mg. of C-076-A1a which is identical with an authentic sample obtained by fermentation.

EXAMPLE 5

22,23 Dihydro C-076 B1a

A. 23-O-[(4-Methylphenoxy)thiocarbonyl]C-076 B2a 4″,5-di-O-acetate

20 Mg. of C-076 B2a 4″,5-di-O-acetate is dissolved in 10 drops of dry pyridine and 2 drops of O-(4-methylphenyl)chlorothioformate is added affording a brownish precipitate which dissolves after stirring for 30 minutes at room temperature. The reaction mixture is stirred an additional 30 minutes and diluted with ice and water and extracted with ether 3 times. The combined organic layers are washed 5 times with water, dried over magnesium sulfate and evaporated under a stream of nitrogen affording 55 mg. of a brown solid, which is dissolved in methylene chloride and placed on a 2000μ preparative layer chromatography plate and eluted with methylene chloride containing 5% tetrahydrofuran and 0.15% ethanol. The slower moving spot affords 13.5 mg. of a light orange solid which is identified as 23-O-[(4-methylphenoxy)thiocarbonyl] C-076 B2a 4″,5-di-O-acetate with 300 mHz nuclear magnetic resonance. The material is used as is in subsequent steps.

B. 22,23-Dihydro C-076 B1a 4″,5-di-O-acetate

10 Mg. of 23-O-[(4-methylphenoxy)thiocarbonyl] C-076 B2a 4″,5-di-O-acetate is dissolved in 0.4 ml. of dry toluene containing 5.2 mg. of tributyltin hydride and 0.15 mg. of azobisisobutyronitrile. The reaction mixture is refluxed for 2 hours whereupon thin layer chromatographic analysis indicates the reaction is not yet completed. An additional portion of 0.2 ml. of tributyltin hydride and 10 mg. azobisisobutyronitrile are added and the refluxing continued for an additional two hours. Thin layer chromatography indicates the reaction is still incomplete and an additional 0.2 ml. of tributyltin hydride and 10 mg. of azobisisobutyronitrile added and refluxing continued for 2 additional hours. Thin layer chromatography indicates the presence of product and the reaction mixture is evaporated under a stream of nitrogen and diluted with methylene chloride and placed on a column of 25 g. of silica gel in methylene chloride. The column is washed with 4 column volumes of methylene chloride to remove impurities and the eluant changed to ethyl acetate to collect the product in 4 column volumes. 10 Mg. of material is removed from the column and dissolved in methylene chloride and placed on a 250μ silica gel preparative layer chromatography plate and eluted twice with methylene chloride containing 4% tetrahydrofuran and 0.15% ethanol. The slower moving band is removed and identified with 300 MHz nuclear magnetic resonance and mass spectrometry as 22,23-dihydro C-076 B1a 4″,5-di-O-acetate.

C. 22,23 Dihydro C-076 B1a

Deprotection of 22,23-dihydro C-076 B1a-4″,5-di-O-acetate with aqueous-methanolic sodium hydroxide solution as described in Example 4B gives 22,23-dihydro C-076 B1a.

EXAMPLE 6

22,23-Dihydro C-076 B1a

A. 4″,5-tert-butyl dimethylsilyl C-076 B2a

250 Mg. of C-076 B1a is dissolved in 2.5 ml. of dry dimethylformamide and combined with 115 mg. of imidazole and 130 mg. of tert-butyl dimethylsilyl chloride. The reaction mixture is stirred at room temperature for 10 hours, diluted with 50 ml. of ether and washed five times with water, dried over magnesium sulfate and evaporated to dryness in vacuo affording 380 mg. of residue. The residue is dissolved in methylene chloride and placed on three 1500μ silica gel preparative layer chromatography plates and eluted with 7% tetrahydrofuran, and 0.2% ethanol in methylene chloride. The middle of the 3 major bands of product is isolated affording 127.7 mg. of a yellow syrup which is identified as 4″,5-tert-butyldimethylsilyl C-076 B2a which is used as is in subsequent steps.

B. 23-O([4-methylphenoxy]thiocarbonyl)-4″,5-di-O-tert-butyl dimethylsilyl C-076 B2a 500 Mg. of 4″,5-di-O-tert-butyl dimethylsilyl C-076 B2a is combined with 2.5 ml. of dry pyridine and stirred while 0.5 ml. of 0-(4-methylphenyl)chlorothioformate is added dropwise. The reaction mixture is stirred at room temperature for 6 hours whereupon water and ether are added and the mixture shaken and the layers separated. The aqueous layer is extracted with ether and the combined organic layers are washed five times with water, dried over magnesium sulfate and evaporated to dryness in vacuo affording 1 g. of a dark brown gum. The residue is dissolved in methylene chloride and placed on five 2000μ silica gel preparative layer chromatography plates and eluted first with methylene chloride to remove impurities and then with 5% ethyl acetate in methylene chloride twice. The two fastest bands of material are separately chromatographed on four 1000μ silica gel preparative layer chromatography plates eluting with 4% ethyl acetate in methylene chloride. The fastest band on each of the two chromatograms are combined affording 210.5 mg. of a reddish brown foam which is identified by 300 mHz nuclear magnetic resonance and mass spectroscopy as 23-O[(4-methylphenoxy)thiocarbonyl]-4",5-di-O-tert-butyl dimethylsilyl C-076 B2a.

C. 4",5-Di-O-tert-butyl dimethylsilyl-22,23-dihydro C-076 B1a

50 Mg. of 4",5-di-O-tert-butyl dimethylsilyl 23-O-[(4-methylphenoxy)thiocarbonyl] C-076 B2a is combined with 0.1 ml. of tributyltin hydride, 5 mg. of azobisisobutylnitrile in 1.6 ml. of toluene and refluxed for 2 hours whereupon an additional 0.1 ml. of tributyltin hydride and 5 mg. of azobisisobutyronitrile is added and refluxing continued for 2 additional hours. The toluene is removed under a stream of nitrogen and diluted with methylene chloride and placed on a column of 25 g. of silica gel and eluted with methylene chloride to remove impurities. The solvent is changed to ethyl acetate, and the product is removed in 3 column volumes affording 50 mg. of a clear glass. The glass is dissolved in methylene chloride and placed on a 1000μ silica gel preparative layer chromatography plate and eluted with 4% ethyl acetate in methylene chloride followed by 6% ethyl acetate in methylene chloride. The fastest major band is removed affording 37.9 mg. of a yellow glass which mass spectrometry and 300 mHz nuclear magnetic resonance indicate as product.

D. 22,23-Dihydro C-076 B1a

A solution of 200 mg. of 4",5-di-O-tert-butyldimethylsilyl-22,23-dihydro-C-076-B1a in 10 ml. of a 0.1% solution of p-toluene sulfonic acid hydrate in methanol is kept 14 hours at ambient temperature. Then it is diluted with ethylacetate, washed with aqueous sodium bicarbonate solution, water, dried and concentrated in vacuo to a liquid glass. This is further purified by chromatography a 1000μ silica gel plate to give 9 mg. of pure 22,23-dihydro C-076-B1a.

EXAMPLE 7

C-076 B1a

A. 4",5-Di-O-tert-butyl dimethylsilyl C-076 B1a

50 Mg. of 4",5-di-O-tert-butyl dimethylsilyl 23-O-[(4-methylphenoxy)thiocarbonyl] C-076 B2a as obtained in Example 6B is combined with 2.5 ml. of 1,2,4 trichlorobenzene and immersed in an oil bath at 200°-210° C. under a nitrogen atmosphere for 45 minutes. The reaction mixture is placed on a column of 30 g. of silica gel and eluted with 3 column volumes of methylene chloride and then with 5% ethyl acetate in methylene chloride followed by 10% ethyl acetate in methylene chloride. The last elution solvent mixture affords 60 mg. of a yellowish film which is dissolved in methylene chloride and placed on two 1000μ silica gel preparative layer chromatography plates and eluted twice with 5% ethyl acetate in methylene chloride affording 19.6 mg. of yellow glass which is identified by mass spectrometry and 300 mHz nuclear magnetic resonance as 4",5-di-O-tert-butyl dimethylsilyl C-076 B1a.

B. C-076-B1a

4",5-Di-O-tert-butyldimethylsilyl C-076-B1a is deprotected as described in Example 6D to give pure C-076-B1a.

EXAMPLE 8

4",5-Di-O-phenoxyacetyl c-076 B2a/B2b

1 G. of C-076 B2a/B2b is dissolved in 10 ml. of methylene chloride which contains 0.25 ml. of pyridine. The solution is placed under nitrogen and cooled in an ice bath. With stirring, 10 ml. of methylene chloride containing 0.39 ml. of phenoxyacetylchloride is added, and the mixture stirred for 1 hour in an ice bath. The reaction mixture is poured onto 100 ml. of ice water and extracted 3 times with ether. The combined ether extracts are washed 3 times with water, once with saturated sodium chloride, dried over magnesium sulfate, and evaporated to dryness in vacuo. The residue is chromatographed on 80 g. of silica gel eluting with 12% ethylacetate in methylene chloride. Fractions 1–10 are discarded; fractions 11–20 afford 49 mg. of a pale yellow film; and fractions 25–72 afford 880 mg. of a white foam which is identified by 300 mHz nuclear magnetic resonance as 4",5-di-O-phenoxyacetyl C-076 B2a/B2b.

EXAMPLE 9

C-076-B1a/B1b

A. 4",5-Di-O-phenoxyacetyl-23-O-[(4-methylphenoxy)-thiocarbonyl] C-076-B2a/B2b

100 Mg. of 4",5-di-O-phenoxyacetyl C-076-B1a/B2b is dissolved in 1.0 ml. of anhydrous pyridine and 0.2 ml. of (4-methylphenyl)chlorothioformate is added at 18° C. and stirred for 16 hours. The reaction mixture is worked up by addition of water and extraction of the product with ether. The ether extract is washed with water, dried over magnesium sulfate, and concentrated under a stream of nitrogen to a brown oil, which is further purified by preparative thin layer chromatography to give pure 4",5-di-O-phenoxyacetyl-23-O-[(4-methylphenoxy)thiocarbonyl] C-076-B2a/B2b characterized by mass spectrometry and nuclear magnetic resonance spectroscopy.

B. 4",5-Di-O-phenoxyacetyl-22,23-dihydro-C-076-B1a/B1b

4",5-Di-O-phenoxyacetyl-23-O[(4-methylphenoxy)-thiocarbonyl] C-076 B2a/B2b is reduced with tributyltin hydride according to Example 1E affording 4",5-di-O-phenoxyacetyl-22,23-dihydro-C-076-B1a/B1b.

C. 22,23-Dihydro-C-076-B1a/B1b

100 Mg. of 4",5-di-O-phenoxyacetyl-22,23-dihydro-C-076 B1a/B1b is dissolved in 2 ml. of methanol. 2 Ml. of a methanol solution previously saturated with ammonia gas at 0° C. is added and the reaction mixture is stirred for 75 minutes at 18° C. The product is isolated by evaporation of the reaction mixture in vacuo at 20° C. dissolved in ether, washed with water dried over magnesium sulfate and concentrated in a stream of nitrogen. The crude product is further purified by thin layer chromatography and the purified product is compared by high pressure liquid chromatography and 300 mHz nuclear magnetic resonance spectrum with authentic material prepared by catalytic hydrogenation of C-076 B1a/B1b.

D. C-076 B1a/B1b

4",5-Di-O-phenoxyacetyl-23-O-[(4-methylphenoxy)-thiocarbonyl] C-076 B2a/B2b is pyrolized as described in Example 2A. The crude 4",5-di-O-phenoxyacetyl-C-076-B1a/B1b is deprotected and purified as described in the previous example to give essentially pure C-076-B1a/B1b.

What is claimed is:

1. A process for converting C-076 A2a/A2b and C-076 B2a/B2b compounds into C-076 A1a/A1b and C-076 B1a/B1b compounds respectively, which comprises reacting a suitably protected C-076 A2a/A2b or C-076 B2a/B2b compound with a substituted thiocarbonyl halide having the formula:

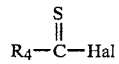

wherein Hal is a halogen selected from fluorine, chlorine, bromine or iodine, and $R_4$ is phenyl; substituted phenoxy wherein the substituents are loweralkyl; or disubstituted amino wherein the substituents are loweralkyl, in the presence of a tertiary amine, to produce the 23-O-(substituted thiocarbonyl) compound which is pyrolyzed by heating neat or in a high boiling solvent at from 150° to 250° C. to eliminate the 23-O-(substituted thiocarbonyl) group and introduce the 22,23-unsaturation; and said C-076 A1a/A1b and C-076 B1a/B1b compounds are prepared by removing any such protecting groups.

2. The process of claim 1 wherein Hal is chlorine.

3. The process of claim 2 wherein Hal is chlorine and $R_4$ is 4-methylphenoxy.

4. The process of claim 1 wherein the tertiary amine is triethylamine, pyridine, dimethyl amino pyridine, or diisopropylethylamine.

5. The process of claim 1 wherein the protecting group is a trisubstituted silyloxy acetyl, a trisubstituted silyl, acyl or substituted acyl.

6. The process of claim 5 wherein the protecting group is tert-butyl dimethylsilyloxyacetyl, a tert-butyl-dimethylsilyl, acetyl, trifluoroacetyl, trichloroacetyl, chloroacetyl, hydroxyacetyl, or phenoxyacetyl.

7. A compound having the formula:

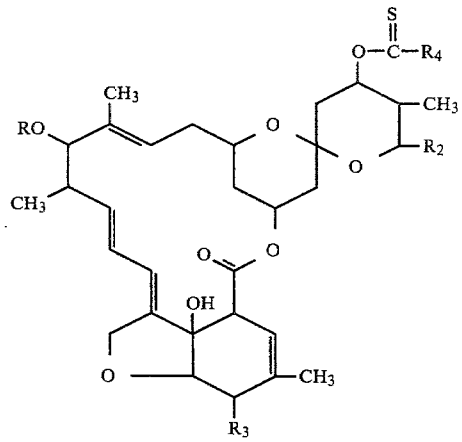

wherein
R is the 4'-(α-L-oleandrosyl)-α-L-oleandrose group;
$R_2$ is iso-propyl or sec-butyl;
$R_3$ is methoxy or hydroxy; and
$R_4$ is substituted phenoxy wherein the substituent is loweralkyl; and the trisubstituted silyloxyacetyl, trisubstituted silyl, loweralkanoyl or substituted loweralkanoyl protected derivative thereof wherein the substituents are trifloro, trichloro, chloro, hydroxy or phenoxy.

* * * * *